United States Patent [19]

Imafuku et al.

[11] Patent Number: 5,814,680
[45] Date of Patent: Sep. 29, 1998

[54] SOFT INTRAOCULAR LENS

[75] Inventors: Suguru Imafuku; Migio Hamano; Hidetoshi Iwamoto, all of Tokyo, Japan

[73] Assignee: Hoya Corporation, Japan

[21] Appl. No.: 606,046

[22] Filed: Feb. 21, 1996

[30] Foreign Application Priority Data

Feb. 23, 1995 [JP] Japan ...................................... 7-35228

[51] Int. Cl.⁶ .................................................. C08F 220/30
[52] U.S. Cl. ........................ 523/106; 526/246; 526/259; 526/301; 526/326; 623/6
[58] Field of Search ............................ 523/106; 526/246, 526/326, 301, 259; 623/6

[56] References Cited

U.S. PATENT DOCUMENTS

| | | | |
|---|---|---|---|
| 4,620,954 | 11/1986 | Singer et al. | 526/264 |
| 4,731,079 | 3/1988 | Stoy | 623/6 |
| 5,264,465 | 11/1993 | Futamura et al. | 523/106 |
| 5,507,804 | 4/1996 | LlaNos | 623/11 |

FOREIGN PATENT DOCUMENTS 0485197  5/1992  European Pat. Off. ............... 526/326

*Primary Examiner*—Andrew E. C. Merriam
*Attorney, Agent, or Firm*—Nixon & Vanderhye

[57] ABSTRACT

A soft intraocular lens consisting of a copolymer formed from a perfluorooctylethyloxypropylene (meth)acrylate monomer, a 2-phenylethyl (meth)acrylate monomer, an alkyl (meth)acrylate monomer and a crosslinking monomer as essential components restores its original shape to stabilize itself in a proper period of time, e.g., approximately 20~60 seconds, without remaining folded or self-adhering in its optical portion when folded to a small size, inserted into the eye while being held in a folded state and then released from a folding force.

7 Claims, 1 Drawing Sheet

SOFT INTRAOCULAR LENS

FIELD OF THE INVENTION

The present invention relates to a soft intraocular lens easily insertable through a small incision. More specifically it relates to a soft intraocular lens which can restore its original shape to stabilize itself in a proper period of time, e.g., approximately 20~60 seconds, without remaining folded (self-adhering) in its optical portion when folded to a small size, inserted into the eye while being held in a folded state and then released from a folding force.

TECHNICAL BACKGROUND

With an increase in the population of the aged, the number of aged patients having senile cataract has noticeably increased. The cataract is treated by removing an opaque nucleus of lens and cortex, and correcting the vision with an ophthalmic lens or a contact lens, or inserting an intraocular lens. It is a generally practiced method at present to remove the lens as a whole and then fix an intraocular lens. The main current of the raw material for the lens is PMMA (polymethyl methacrylate) having excellent biocompatibility and processability.

On the other hand, as ultrasonic emulsification suction has come into wide use in recent years, small incisions are widely operated for decreasing post-operation astigmatism. Most of lenses for a small incision operation appear to be lenses formed of a silicone which has results as a coating agent or a reconstructive mammaplasty material. However, a silicone lens has property problems in that it is difficult to fold and fix it so that it requires a special injector, and that its power to restore the shape from a folded state is so high that it is liable to injure intracystic cells. Further, the silicon lens also involves various problems that cells are scarcely fused to it so that its intracystic fixing is insufficient and that it causes inflammation and opacity relatively frequently after operation.

For overcoming the above defects of the silicon lens, JP-A-4-292609 discloses a soft intraocular lens of a copolymer formed from at least two arylalkyl (meth)acrylates and a crosslinking monomer as monomer components.

The soft intraocular lens disclosed in the above patent publication has a high refractive index so that its thickness can be advantageously decreased. However, when the lens is folded in two, the two portions of its optical portion remain attached to each other or are difficult to detach from each other. The above soft intraocular lens therefore has a defect in that the manual operation of inserting it into the eye is difficult.

Meanwhile, U.S. Pat. No. 5,331,073 in Example 1 discloses an intraocular lens of a copolymer formed from phenoxyethyl acrylate, n-hexyl acrylate and ethylene glycol dimethacrylate of a crosslinking monomer as monomer components. However, the intraocular lens disclosed in Example 1 of the above U.S. Patent has a defect in that it is liable to injure intracystic cells since it recovers its original shape in a few seconds after folded in two, i.e., recovers its original shape too quickly.

DISCLOSURE OF THE INVENTION

It is an object of the present invention to provide a soft intraocular lens which can restore its original shape to stabilize itself in a proper period of time, e.g., approximately 20~60 seconds, without remaining folded (self-adhering) in its optical portion when folded to a small size, inserted into the eye while being held in a folded state and then released from a folding force.

The present inventor has diligently studied to achieve the above object and has found that a soft intraocular lens consisting of a copolymer obtained by copolymerizing a specific monomer mixture solution containing a monomer of the following general formula (I), a monomer of the following general formula (II), a monomer of the following general formula (III) and a crosslinking monomer has flexibility adequate for folding, is free from remaining folded (self-adhering) in its optical portion when folded to a small size such that the optical portion is in self-contact, and restores its original shape to stabilize itself in a proper period of time, e.g., approximately 20~60 seconds, when released from a folding force.

The present invention has been made on the basis of the above finding, and the gist of the present invention consists in a soft intraocular lens consisting of a copolymer formed from a perfluorooctylethyloxypropylene (meth)acrylate of the general formula (I),

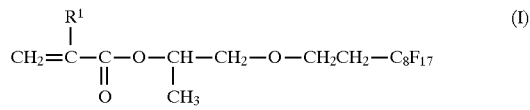

wherein $R^1$ is hydrogen or methyl, a 2-phenylethyl (meth)acrylate monomer of the general formula (II),

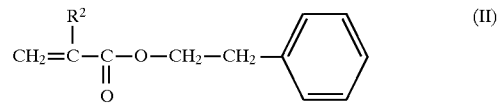

wherein $R^2$ is hydrogen or methyl, an alkyl (meth)acrylate monomer of the general formula (III),

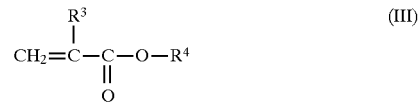

wherein $R^3$ is hydrogen or methyl and $R^4$ is a linear or branched $C_4$~$C_{12}$ alkyl group, and a crosslinking monomer as essential monomer components.

PREFERRED EMBODIMENTS OF THE INVENTION

Figure 1:
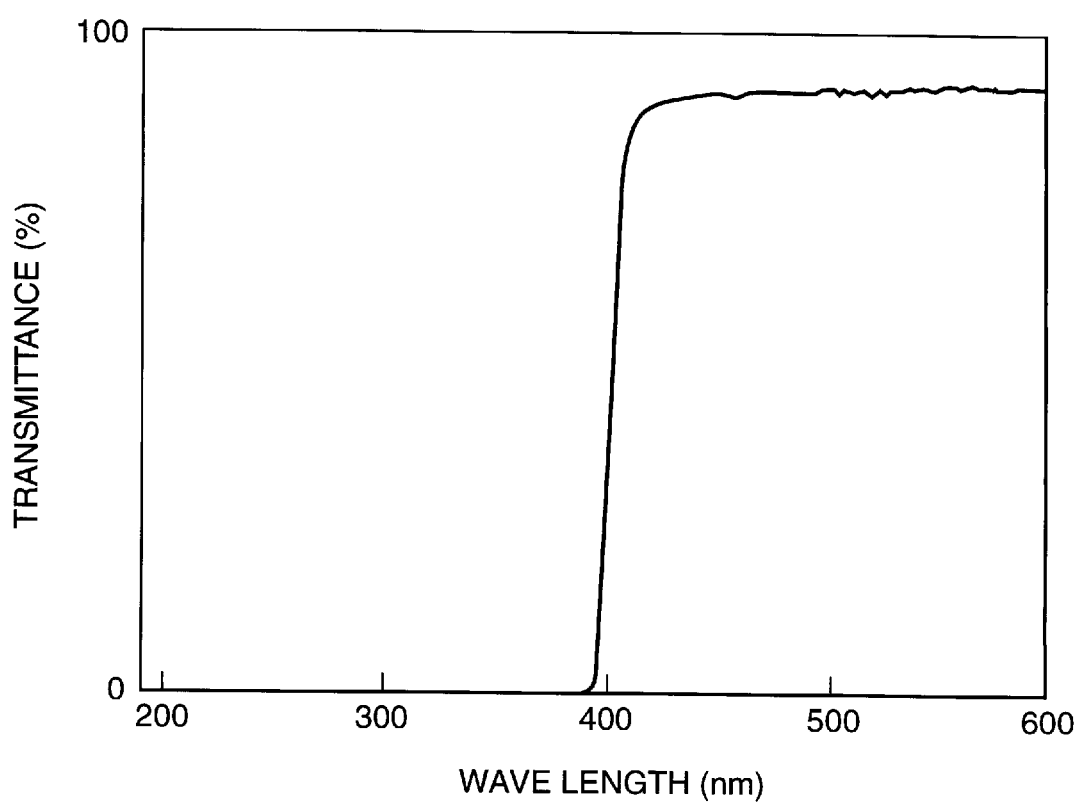
FIG. 1 shows the transmittance curve of an intraocular lens consisting of a copolymer obtained in Example 1 in an ultraviolet region.

The present invention will be specifically explained hereinafter.

The first monomer component for constituting the soft intraocular lens of the present invention is a perfluorooctylethyloxypropylene (meth)acrylate of the above general formula (I), and it is an important component for decreasing the surface self-adhering property of the soft intraocular lens material and imparting the material with the function of the lens restoring its original shape to stabilize itself in a proper period of time, e.g., approximately 20~60 seconds.

In the above general formula (I), $R^1$ is hydrogen or methyl, preferably methyl.

In the present invention, the monomer of the general formula (I) can be added in an amount, preferably, in the range of from 5 to 20% by weight, more preferably 7 to 15% by weight. When the amount of the monomer (I) is less than 5% by weight, undesirably, it is difficult to produce sufficient effects of decreasing the surface self-adhering property and restoring the original shape to stableness in a proper period of time, e.g., approximately 20 to 60 seconds. When it exceeds 20% by weight, undesirably, the property of the soft intraocular lens restoring its original shape is liable to decrease.

The second monomer component for constituting the soft intraocular lens of the present invention is a 2-phenylethyl (meth)acrylate of the general formula (II), and it is an essential component for imparting the soft intraocular lens material with a high refractive index.

In the above general formula (II), $R^2$ is hydrogen or methyl, preferably methyl.

In the present invention, the monomer of the general formula (II) can be added in an amount preferably in the range of from 40 to 60% by weight, more preferably 42 to 56% by weight. When the amount of the monomer (II) is less than 40% by weight, undesirably, it is difficult to impart the lens material with a sufficient refractive index. When it exceeds 60% by weight, undesirably, the soft intraocular lens no longer has flexibility and it is difficult to fold it to a small size, although its refractive index is high.

The third monomer component for constituting the soft intraocular lens of the present invention is an alkyl (meth) acrylate of the general formula (III), and it is an essential component for imparting the soft intraocular lens with flexibility.

In the above general formula (III), $R^3$ is hydrogen or methyl, preferably hydrogen, and $R^4$ is a linear or branched $C_4$~$C_{12}$ alkyl group. Specific examples of the monomer of the general formula (III) include n-butyl acrylate, isobutyl acrylate, isoamyl acrylate, hexyl acrylate, 2-ethylhexyl acrylate, octyl acrylate, isooctyl acrylate, decyl acrylate, isodecyl acrylate, and the like.

The monomer of the general formula (III) can be added in an amount, preferably in the range of from 30 to 50% by weight, more preferably 35 to 46% by weight. When the amount of the monomer (III) is less than 30% by weight, undesirably, it is difficult to impart the lens material with flexibility. When it exceeds 50% by weight, undesirably, the surface self-adhering property of the lens material increases.

The fourth component for constituting the soft intraocular lens of the present invention is a crosslinking monomer, and a single monomer or a mixture of at least two monomers is used as such. The crosslinking monomer is an essential component for preventing the plastic deformation of the lens and further improving the lens in mechanical strength. Examples thereof include ethylene glycol dimethacrylate (to be referred to as "EDMA" hereinafter), diethylene glycol dimethacrylate, triethylene glycol dimethacrylate, tetraethylene glycol dimethacrylate, 1,4-butanediol methacrylate, 1,4-butanediol diacrylate and 1,6-hexanediol dimethacrylate.

The amount of the crosslinking monomer is preferably 0.5 to 4% by weight, particularly preferably 1 to 3.5% by weight, based on the total amount of the monomers of the general formulae (I), (II) and (III). When the amount of the crosslinking monomer is less than 0.5% by weight, undesirably, the effect produced by the introduction of the crosslinking monomer is hardly found. When it exceeds 4% by weight, undesirably, the number of crosslinking points is large so that the copolymer is fragile and the lens is liable to show decreased mechanical strength.

In the present invention, a monomer having the capability of ultraviolet light absorption may be used as a component for constituting the soft intraocular Lens in addition to the above essential components. A monomer of the following general formula (IV), having the capability of ultraviolet light absorption, is one example thereof.

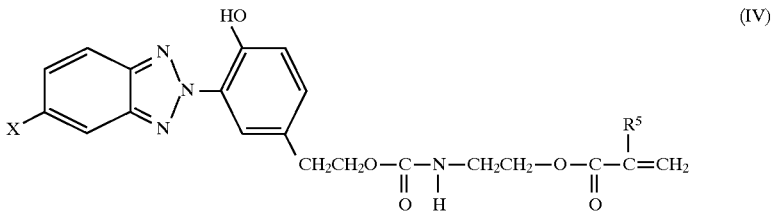

wherein X is a hydrogen atom or a chlorine atom and $R^5$ is hydrogen or methyl.

Specific examples of the monomer of the general formula (IV), having the capability of ultraviolet light absorption, include 5-chloro-2-[2-hydroxy-5-(β-methacryloyloxyethylcarbamoyloxyethyl)]phenyl-2H-benzotriazole (to be referred to as "CHMP" hereinafter), and 2-[2-hydroxy-5-(β-methacryloyloxyethylcarbamoyloxyethyl)]phenyl-2H-benzotriazole.

The amount of the monomer having the capability of ultraviolet light absorption is preferably, 0.05 to 3% by weight, particularly preferably 0.1 to 2% by weight, based on the total amount of the monomers of the general formulae (I), (II) and (III). When the above amount is less than 0.05% by weight, there is almost no effect on the prevention of ultraviolet light. When it exceeds 3% by weight, there is not any further remarkable effect on the prevention of ultraviolet light.

For coloring the soft intraocular lens material, other comonomer such as a polymerizable dyestuff may be used.

The process for the production of the intraocular lens of the present invention will be explained hereinafter.

When the copolymer for constituting the soft intraocular lens of the present invention is produced, a polymerization initiator is added to a mixture of the above monomers, the mixture is fully stirred to form a homogeneous mixture solution, and then the mixture solution is polymerized by a conventional method. The conventional method refers to a method in which, after the addition of a radical polymerization initiator, the mixture is stepwise or continuously temperature-increased in a temperature range of from 40° to 120° C., or the mixture is irradiated with ultraviolet light or visible light.

Specific examples of the above radical polymerization initiator include azo initiators such as azobisvaleronitrile and azobisisobutyronitrile (to be referred to as "AIBN" hereinafter) and organic peroxides such as bis(4-tert-butylcyclohexyl)peroxycarbonate. The amount of the above initiator is preferably approximately 0.05 to 0.5% by weight based on the total amount of the monomers.

The copolymer for constituting the soft intraocular lens of the present invention can be shaped into an intraocular lens form by a mold method in which a mixture of the above monomers is charged into a mold having a cavity with an inner surface corresponding to a form of an intended intraocular lens to obtain a molded article, or by a method in which the polymerization is carried out in a proper mold or container to obtain a copolymer in the form of a rod, a block or a plate and then the copolymer is cut and milled at a low temperature.

Further, for obtaining the intraocular lens, a lens support portion may be prepared separately from a lens and then attached to the lens, or the lens support portion may be shaped integrally with the lens. The material for the support portion is selected from a material such as polypropylene and PMMA.

The soft intraocular lens of the present invention has the following self-adhering property, capability of restoring its original shape and folding strength, of which the measurement methods are explained in Examples.

Self-adhering property: When an optical portion is held with an intraocular lens insertion device, folded and released at room temperature of 36° C., the lens does not remain folded (self-adhering) in the optical portion.

Capability of restoring original shape: 20~60 seconds

Folding load: 100~300 g

EXAMPLE

The present invention will be further explained with reference to Examples hereinafter, while the present invention shall not be limited to these Examples.

Example 1

An ampoule tube having a volume of 30 ml was charged with 0.48 g (8 wt %) of perfluorooctylethyloxypropylene methacrylate (BRM), 3 g (50 wt %) of 2-phenylethyl methacrylate (PEMA), 2.52 g (42 wt %) of butyl acrylate (BA), 0.03 g (0.5 wt % based on the total amount of BRM, PEMA and BA) of 5-chloro-2[2-hydroxy-5-(β-methacryloyloxyethylcarbamoyloxy-ethyl)]phenyl-2H-benzotriazole (CHMP), 0.18 g (3 wt % based on the total amount of BRM, PEMA and BA) of ethylene glycol dimethacrylate and 0.012 g (0.2 wt % based on the total amount of BRM, PEMA and BA) of AIBN, and the mixture was fully stirred to obtain a homogeneous monomer mixture solution. The solution was cast into a shaping mold prepared by sandwiching a Teflon frame (1 mm thick) with glass plates (1.3 mm thick each) and into a shaping mold for manufacturing an intraocular lens, formed of polypropylene. The two shaping molds were placed in a pressure polymerization furnace, and each solution was polymerized in a nitrogen atmosphere at a pressure of 2 kgf/cm$^2$ at a temperature of 110° C. for 2 hours, to give a copolymer in the form of a film and a copolymer in the form of optical portion of an intraocular lens. The obtained copolymers were immersed in 100 ml of methanol to remove unreacted monomers and then fully dried to prepare test samples, and the test samples were measured for various physical properties. The physical properties were measured as follows.

1. Appearance

A test sample was evaluated for transparency and discoloration by visually observing the test sample in water.

[Ratings of Evaluation]

O: Colorless and transparent

Δ: Slightly opaque

X: Opaque

2. Self-adhering property

A copolymer in the form of optical portion of an intraocular lens was held with an intraocular lens insertion device and released from the holding force in a room at 36° C. At this time, the optical portion was observed for a self-adhering property.

[Evaluation ratings]

O: Not at all self-adhering in optical portion.

Δ: Two parts of an optical portion adhered to each other and came apart from each other after some time.

X: Two parts of an optical portion adhered to each other and did not come apart from each other.

3. A copolymer in the form of a film (10 mm long, 5 mm wide and about 1 mm thick) was folded in two, and measured for a time until it restored its original shape (unit: second).

4. Folding load

A copolymer in the form of a film (10 mm long, 5 mm wide and about 1 mm thick) was folded with a universal material tester supplied by Instron Japan K. K., and the copolymer was measured for a folding load. The folding rate was set at 100 mm/minute, the folding distance was set at 6 mm, and a force at this time was used as an index for a force required for folding the copolymer (unit: g).

5. Refractive index

A test sample was measured for a refractive index for e-ray (546.1 nm) at 36° C. with a refractometer supplied by Atago K. K.

Table 1 shows the results of measurements of the physical properties. Table 1 shows that the copolymer obtained in this Example 1 had no self-adhering property, showed a small folding load (easy foldability) and restored its original shape in about 30 seconds. Further, the intraocular lens of the copolymer obtained in this Example 1 was excellent in the effect of ultraviolet light prevention due to the introduction of CHMA having the capability of ultraviolet light absorption. 1 Gram of small pieces of this copolymer were immersed in 50 ml of distilled water and heated at 100° C. for 30 minutes for extraction, while no elution of CHMP was found. FIG. 1 shows the absorption curve of the intraocular lens of the copolymer obtained in Example 1 in an ultraviolet light region.

Examples 2~4

AIBN was added to a monomer mixture solution of BRM, PEMA, BA, CHMP and EDMA, and the mixture was polymerized, in the same manner as in Example 1, to give copolymers. Table 1 shows amounts of the polymerizable monomers, crosslinking monomers and radical polymerization initiators. Then, non-polymerized monomers were removed in the same manner as in Example 1, and the copolymers were measured for various physical properties. Table 1 shows the results. The intraocular lenses of the copolymers obtained in these Examples had no self-adhering property, showed a small folding load (easy foldability), and restored their original shapes in approximately 25 to 40 seconds. Further, the intraocular lenses of the copolymers obtained in these Examples were excellent in the effect of ultraviolet light prevention due to the introduction of CHMA.

Example 5

An ampoule tube having a volume of 30 ml was charged with 0.6 g (10 wt %) of BRM, 3 g (50 wt %) of PEMA, 2.4 g (40 wt %) of 2-ethylhexyl acrylate (to be referred to as "EHA" hereinafter), 0.03 g (0.5 wt % based on the total amount of BRM, PEMA and EHA) of CHMP, 0.18 g (3 wt % based on the total amount of BRM, PEMA and EHA) of EDMA and 0.012 g (0.2 wt % based on the total amount of BRM, PEMA and EHA) of AIBN, and the mixture was fully stirred to obtain a homogeneous monomer mixture solution. The solution was cast into a shaping mold prepared by sandwiching a Teflon frame (1 mm thick) with glass plates (1.3 mm thick each) and into a shaping mold for manufacturing an intraocular lens, formed of polypropylene. The two shaping molds were placed in a pressure polymerization furnace, and each solution was polymerized in a nitrogen atmosphere at a pressure of 2 kgf/cm$^2$ at a temperature of 110° C. for 2 hours, to give a copolymer in the form of a film and a copolymer in the form of optical portion of an intraocular lens. The so-obtained copolymers were immersed in 100 ml of methanol to remove unreacted monomers and then fully dried to prepare test samples, and the test samples were measured for various physical properties. Table 1 shows the results. The intraocular lenses of the copolymers obtained in these Examples had no self-adhering property, showed a small folding load (easy foldability), and restored their original shapes in approximately 25 to 40 seconds. Further, the intraocular lenses of the copolymers obtained in these Examples were excellent in the effect of ultraviolet light prevention due to the introduction of CHMA.

Examples 6~7

AIBN was added to a monomer mixture solution containing BRM, PEMA, EHA, CHMP and EDMA, and the mixture solution was polymerized, in the same manner as in Example 5, to obtain a copolymer. Table 1 shows the amounts of the polymerizable monomers, crosslinking monomer and radical polymerization initiator. Then, unreacted monomers were removed, and the copolymers were measured for various physical properties, in the same manner as in Example 5. Table 1 shows the results. The intraocular lenses of the copolymers obtained in these Examples had no self-adhering property, showed a small folding load (easy foldability), and restored their original shapes in approximately 30 to 50 seconds. Further, the intraocular lenses of the copolymers obtained in these Examples were excellent in the effect of ultraviolet light prevention due to the introduction of CHMA.

Comparative Example 1

An ampoule tube having a volume of 30 ml was charged with a monomer mixture solution containing 3.264 g (54.4 wt %) of PEMA, 2.736 g (45.6 wt %) of BA and 0.18 g (3 wt % based on the total amount of PEMA and BA), and 0.012 g (0.2 wt % based on the total amount of PEMA and BA) of AIBN was added. The monomer mixture solution was polymerized to give a copolymer. Then, unreacted monomers were removed in the same manner as in Example 1, and the copolymer was measured for various physical properties. Table 1 shows the results. When the copolymer in the form of optical portion of an intraocular lens was held with an intraocular lens insertion device and released from the holding force in a room at 36° C., the optical portion showed the self-adhering property.

Comparative Example 2

A copolymer was obtained in the same manner as in Example 1 except that 2,2,2-trifluoroethyl methacrylate (to be referred to as "TFEMA" hereinafter) was used in place of BRM (no CHMP was introduced). That is, to a monomer mixture solution containing 0.48 g (8 wt %) of TFEMA, 3 g (50 wt %) of PEMA, 2.52 g (42 wt %) of BA and 0.18 g (3 wt % based on the total amount of TFEMA, PEMA and BA) of EDMA was added 0.012 g (0.2 wt % based on the total amount of TFEMA, PEMA and BA) of AIBN, and the resultant monomer mixture solution was polymerized to obtain a copolymer. Then, unreacted monomers were removed in the same manner as in Example 1, and the copolymer was measured for various physical properties. Table 1 shows the results. The copolymer obtained in this Comparative Example 2 showed a large folding load (hard foldability) as compared with the polymer obtained in Example 1, and that the recovery of the original shape was extremely slow.

Comparative Example 3

A copolymer was obtained in the same manner as in Example 1 except that methyl methacrylate (to be referred to as "MMA" hereinafter) was used in place of BRM (no CHMP was introduced). That is,to a monomer mixture solution containing 0.48 g (8 wt %) of MMA, 3 g (50 wt %) of PEMA, 2.52 g (42 wt %) of BA and 0.18 g (3 wt % based on the total amount of MMA, PEMA and BA) of EDMA was added 0.012 g (0.2 wt % based on the total amount of MMA, PEMA and BA) of AIBN, and the resultant monomer mixture solution was polymerized to obtain a copolymer. Then, unreacted monomers were removed in the same manner as in Example 1, and the copolymer was measured for various physical properties. Table 1 shows the results. The copolymer obtained in this Comparative Example 3 showed a large folding load (hard foldability) as compared with the polymer obtained in Example 1, and that the recovery of the original shape was extremely slow.

Comparative Example 4

A copolymer was obtained in the same manner as in Example 5 except that TFEMA was used in place of BRM (no CHMP was introduced). That is, to a monomer mixture solution containing 0.6 g (10 wt %) of TFEMA, 3 g (50 wt %) of PEMA, 2.4 g (40 wt %) of EHA and 0.18 g (3 wt % based on the total amount of TFEMA, PEMA and EHA) of EDMA was added 0.012 g (0.2 wt % based on the total amount of TFEMA, PEMA and EHA) of AIBN, and the resultant monomer mixture solution was polymerized to obtain a copolymer. Then, unreacted monomers were removed in the same manner as in Example 5, and the copolymer was measured for various physical properties. Table 1 shows the results. The copolymer obtained in this Comparative Example 4 showed a large folding load (hard foldability) as compared with the polymer obtained in Example 5, and that the recovery of the original shape was extremely slow.

Comparative Example 5

A copolymer was obtained in the same manner as in Example 5 except that MMA was used in place of BRM (no CHMP was introduced). That is, to a monomer mixture solution containing 0.6 g (10 wt %) of MMA, 3 g (50 wt %) of PEMA, 2.4 g (40 wt %) of EHA and 0.18 g (3 wt % based on the total amount of MMA, PEMA and EHA) of EDMA was added 0.012 g (0.2 wt % based on the total amount of MMA, PEMA and EHA) of AIBN, and the resultant monomer mixture solution was polymerized to obtain a copolymer. Then, unreacted monomers were removed in the same manner as in Example 5, and the copolymer was measured for various physical properties. Table 1 shows the results. The copolymer obtained in this Comparative Example 5 showed a large folding load (hard foldability) as compared with the polymer obtained in Example 5, and that the recovery of the original shape was extremely slow.

Comparative Example 6

An ampoule tube having a volume of 30 ml was charged with a monomer mixture solution containing 1.83 g (30.5 wt %) of PEMA, 3.972 g (66.2 wt %) of 2-phenylethyl acrylate (to be referred to as "PEA" hereinafter) and 0.198 g (3.3 wt %) of 1,4-butanediol diacrylate (to be referred to as "BDDA" hereinafter), and 0.012 g (0.2 wt % based on the total amount of PEMA, PEA and BDDA) of AIBN was added. The monomer mixture solution was polymerized to give a copolymer. Then, unreacted monomers were removed in the same manner as in Example 1, and the copolymer was measured for various physical properties. Table 1 shows the results. When the copolymer in the form of optical portion of an intraocular lens was held with an intraocular lens insertion device and released from the holding force in a room at 36° C., the optical portion showed the self-adhering property.

TABLE 1

| | Example | | | | |
|---|---|---|---|---|---|
| | 1 | 2 | 3 | 4 | 5 |
| Composition | | | | | |
| BRM | 8 | 8 | 10 | 15 | 10 |
| PEMA | 50 | 46 | 49 | 46.2 | 50 |
| BA | 42 | 46 | 41 | 38.0 | |
| PEA | | | | | |
| PHA | | | | | 40 |
| TFEMA | | | | | |
| MMA | | | | | |
| CHMP | 0.5 | 0.5 | 0.5 | 0.5 | 0.5 |
| EDMA | 3 | 3 | 3 | 3 | 3 |
| BDDA | | | | | |
| AIBN | 0.2 | 0.2 | 0.2 | 0.2 | 0.2 |
| TCP | | | | | |
| Appearance | ○ | ○ | ○ | ○ | ○ |
| Self-adhering property | ○ | ○ | ○ | ○ | ○ |
| Capability of recovering original shape (sec) | 30 | 25 | 33 | 40 | 30 |
| Folding load (g) | 187 | 115 | 205 | 249 | 121 |
| Refractive index | 1.506 | 1.504 | 1.502 | 1.497 | 1.504 |

| | Example | | Comparative Example | |
|---|---|---|---|---|
| | 6 | 7 | 1 | 2 |
| Composition | | | | |
| BRM | 8 | 15 | | |
| PEMA | 55 | 47.2 | 54.4 | 50 |
| BA | | | 45.6 | 42 |
| PEA | | | | |
| PHA | 37 | 37.8 | | |
| TFEMA | | | | 8 |
| MMA | | | | |
| CHMP | 0.5 | 0.5 | | |
| EDMA | 3 | 3 | 3 | 3 |
| BDDA | | | | |
| AIBN | 0.2 | 0.2 | 0.2 | 0.2 |
| TCP | | | | |
| Appearance | ○ | ○ | ○ | ○ |
| Self-adhering property | ○ | ○ | Δ | ○ |
| Capability of recovering original shape (sec) | 45 | 38 | 23 | 90 |
| Folding load (g) | 280 | 156 | 193 | 716 |
| Refractive index | 1.510 | 1.497 | — | — |

| | Comparative Example | | | |
|---|---|---|---|---|
| | 3 | 4 | 5 | 6 |
| Composition | | | | |
| BRM | | | | |
| PEMA | 50 | 50 | 50 | 30.5 |
| BA | 42 | | | |
| PEA | | | | 66.2 |
| PHA | | 40 | 40 | |
| TFEMA | | 10 | | |
| MMA | 8 | | 10 | |
| CHMP | | | | |
| EDMA | 3 | 3 | 3 | |
| BDDA | | | | 3.3 |
| AIBN | 0.2 | 0.2 | 0.2 | |
| TCP | | | | 0.2 |
| Appearance | ○ | ○ | ○ | ○ |
| Self-adhering property | ○ | ○ | ○ | Δ |
| Capability of recovering | 150 | 75 | 120 | 25 |

TABLE 1-continued

| | | | | |
|---|---|---|---|---|
| original shape (sec) | | | | |
| Folding load (g) | 775 | 502 | 596 | 205 |
| Refractive index | — | — | — | — |

As shown in Table 1, the materials in Comparative Examples 1 and 6 showed the self-adhering property, and parts of the optical portion of each of them would not part from each other when the lenses are completely folded in two.

The materials in Comparative Examples 2 to 5 showed decreased surface self-adhering property, while they showed high folding loads (they were difficult to fold) and the recovery of their original shapes was extremely slow.

In contrast, the soft intraocular lens of each of the Examples 1 to 7 had no surface self-adhering property, its original shape to stabilize itself approximately in 20~60 seconds when released from a holding force. The reason therefor was particularly as follows. Due to the introduction fluorooctylethyloxypropylene (meth)acrylate, the surface self-adhering property of the lens materials decreased, and further, there was produced an effect of recovering original shapes at a proper rate without increasing the folding load.

The soft intraocular lens of the present invention restores its original shape to stabilize itself in a proper period of time, e.g., approximately 20~60 seconds, without remaining folded (self-adhering) in its optical portion when folded to a small size, inserted into the eye while being held in a folded state and then released from a folding force. Therefore, it has an effect that it can be assimilated in the eye without injuring intracystic cells.

What is claimed is:

1. A soft intraocular lens consisting of a copolymer formed from 5 to 20% by weight of a perfluorooctylethyloxypropylene (meth)acrylate monomer of the general formula (I),

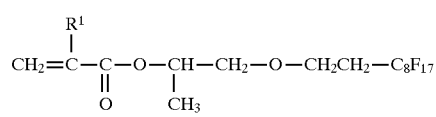

wherein $R^1$ is hydrogen or methyl, 40 to 60% by weight of a 2-phenylethyl (meth)acrylate monomer of the general formula II,

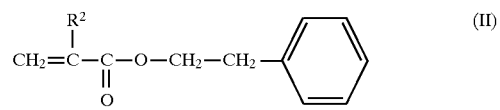

wherein $R^2$ is hydrogen or methyl, 30 to 50% by weight of an alkyl (meth)acrylate monomer of the general formula (III),

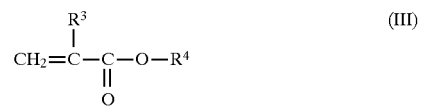

wherein $R^3$ is hydrogen or methyl and $R^4$ is a linear or branched $C_4$–$C_{12}$ alkyl group, and 0.5 to 4% by weight, based upon the total of monomers (I), (II) and (III), of a crosslinking monomer as essential monomer components.

2. The soft intraocular lens of claim 1, wherein the monomer of the general formula (III) is at least one selected from the group consisting of n-butyl acrylate, isobutyl acrylate, isoamyl acrylate, hexyl acrylate, 2-ethylhexyl acrylate, octyl acrylate, isooctyl acrylate, decyl acrylate and isodecyl acrylate.

3. The soft intraocular lens of claim 1, wherein the crosslinking monomer of the general formula (IV) is at least one selected from the group consisting of ethylene glycol dimethacrylate, diethylene glycol dimethacrylate, triethylene glycol dimethacrylate, tetraethylene glycol dimethacrylate, 1-4-butane diol dimethacrylate, 1,4-butane diol diacrylate and 1,6-hexane diol dimethacrylate.

4. The soft intraocular lens of claim 1, wherein the copolymer further contains a monomer capable of ultraviolet light absorption as a monomer.

5. The soft intraocular lens of claim 4, wherein the copolymer contains 0.05 to 3% by weight, based on the total amount of the monomers of the general formulae (I), (II) and (III), of the monomer capable of ultraviolet light absorption.

6. The soft intraocular lens of claim 4 or 5, wherein the monomer capable of ultraviolet light absorption is a compound of the general formula (IV),

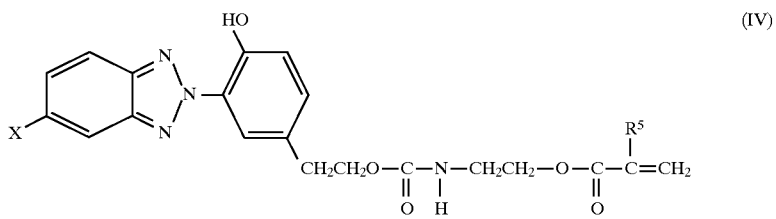

wherein X is a hydrogen atom or a chlorine atom and $R^5$ is hydrogen or methyl.

7. The soft intraocular lens of claim 6, whether the compound of the general formula(IV) is at least one selected from the group consisting of 5-chloro-2-[2-hydroxy-5-(β-methacryloyloxyethylcarbamoyloxyethyl)]phenyl-2H-benzotriazole and 2-[2-hydroxy-5-(Δ-methacryloyloxyethyl-carbamoyloxyethyl)] phenyl-2H-benzotriazole.

* * * * *